US007160982B2

(12) United States Patent
Roques et al.

(10) Patent No.: US 7,160,982 B2
(45) Date of Patent: Jan. 9, 2007

(54) PEPTIDE SUBSTRATE IDENTIFIED BY TYPE BONT/B BOTULINUS TOXIN AND USE THEREOF FOR ASSAYING AND/OR DETECTING SAID TOXIN OR CORRESPONDING INHIBITORS

(75) Inventors: Bernard Roques, Paris (FR); Christine Anne, Chatenay Malabry (FR)

(73) Assignee: Institut National de la Sante et de la Recherche Medicale (Inserm), Paris (FR)

( * ) Notice: Subject to any disclaimer, the term of this patent is extended or adjusted under 35 U.S.C. 154(b) by 291 days.

(21) Appl. No.: 10/296,396

(22) PCT Filed: May 31, 2001

(86) PCT No.: PCT/FR01/01698

§ 371 (c)(1),
(2), (4) Date: Sep. 12, 2003

(87) PCT Pub. No.: WO01/92312

PCT Pub. Date: Dec. 6, 2001

(65) Prior Publication Data

US 2004/0126810 A1    Jul. 1, 2004

(30) Foreign Application Priority Data

Jun. 2, 2000    (FR) .................... 00 07113

(51) Int. Cl.
| C07K 2/00 | (2006.01) |
| C07K 14/00 | (2006.01) |
| C07K 7/08 | (2006.01) |
| G01N 33/533 | (2006.01) |
| C07K 1/00 | (2006.01) |

(52) U.S. Cl. .............. 530/300; 530/324; 530/326; 530/333; 435/4; 435/7.72

(58) Field of Classification Search ............ None
See application file for complete search history.

(56) References Cited

U.S. PATENT DOCUMENTS 4,698,327 A  * 10/1987  Nagarajan et al. ............ 514/8

5,962,637 A  * 10/1999  Shone et al. ................ 530/329
2003/0143651 A1 *  7/2003  Steward et al. ............ 435/7.32

FOREIGN PATENT DOCUMENTS

WO      WO 95 33850 A      12/1995

OTHER PUBLICATIONS

C. Anne, et al. Anal. Biochem. (2001) 291, 253-261, published online Mar. 9, 2001.*
J. Rudinger. In: Peptide Hormones, JA Parsons, Ed. (1976) 1-7.*
W.S. Messer, "Vasopressin and Oxytocin", web document updated Apr. 3, 2000; <http://www.neurosci.pharm.utoledo.edu/MBC3320/vasopressin.htm>; 5 pages.*
S. Rudikoff, et al. Proc. Natl. Acad. Sci. USA (1982) 79, pp. 1979-1983.*
S.-Y. Hua, and M.P. Charlton. Nature Neurosci. (1999) 2(12), pp. 1078-1083.*
D. Voet and J.G. Voet. Biochemistry, 2nd Edition.(1995), pp. 235-241.*
D.E. Smilek, et al. Proc. Natl. Acad. Sci. USA (1991) 88, pp. 9633-9637.*
Soleilhac et al.: "A sensitive and rapid fluorescence-based assay for determination of tetanus toxin peptidase activity," Analytical Biochemistry, vol. 241, 1996, pp. 120-127.
Fitzgerald et al.: "A continuous fluorometric assay for the feline immunodeficiency virus protease," Analytical Biochemistry, vol. 54, Dec. 15, 1997, pp. 226-230.
Peranteau et al.: "Increase in fluorescence upon the hydrolysis of tyrosine peptides: Application to proteinase assays," Analytical Biochemistry, vol. 227, No. 1, 1995, pp. 242-245.
Martin et al.: "Metallopeptidase inhibitors of tetanus toxin: A combinatorial approach," Journal of Medical Chemistry, vol. 42, 1999, pp. 515-525.

* cited by examiner

*Primary Examiner*—Cecilla J. Tsang
*Assistant Examiner*—Andrew D. Kosar
(74) *Attorney, Agent, or Firm*—B. Aaron Schulman; Stites & Harbison PLLC (57) ABSTRACT

A peptide substrate is identified by type BoNT/B botulinus toxin, characterized in that it incorporates in its structure a fragment of formula PYA-(Z)-pNF, wherein Z represents one or several amino acids, said fragment being cleavable by said toxin.

6 Claims, 4 Drawing Sheets

PEPTIDE SUBSTRATE IDENTIFIED BY TYPE BONT/B BOTULINUS TOXIN AND USE THEREOF FOR ASSAYING AND/OR DETECTING SAID TOXIN OR CORRESPONDING INHIBITORS

FIELD OF THE INVENTION

The present invention relates to a method for detecting, identifying and/or characterizing *botulinum* toxin type B or inhibitors and/or activators of said toxin.

BACKGROUND OF THE INVENTION

*Botulinum* neurotoxin type B (BoNT/B) is part of a family of seven structurally related proteins (*botulinum* toxins A to G) produced by various strains of the anaerobic bacillus "*clostridium botulinum*". The two most commonly encountered forms are *botulinum* toxins type A and B. *Botulinum* neurotoxins are the most powerful known toxins, with lethal dose 50s in mice of the order of 0.1 to 0.3 ng/kg. They act on the peripheral nervous system of humans and of various animal species, inducing "botulism", which is characterized by flaccid paralysis of the skeletal muscles, leading to death.

The major form of poisoning with these toxins is due to ingestion of contaminated food. These proteins may constitute a potential biological weapon since they are easy to produce. Finally, for several years, *botulinum* toxins type A and also type B have also been used for therapeutic applications, in the context of dystonias and of motoneuronal hyperactivity, such as strabismus or blepharospasm.

*Botulinum* neurotoxins consist of two subunits: a heavy chain (~100 $k_DA$) linked to a light chain (~50 $k_DA$) by a disulfide bridge. The heavy chain is involved in binding of the toxin to the nerve ending, in internalization and then in translocation of the light chain in the cytosol. The light chain is responsible for the toxicity of the protein by inhibiting $Ca^{2+}$-dependent release of acetylcholine. The light chain can only express its toxicity when it is separated (reduction of the disulfide bridge) from the heavy chain, but it is not capable of penetrating alone into nerve endings (Montecucco et al. (1994) *FEBS Lett*. 346, 92–98).

The toxicity of the light chain of these toxins is due to its peptidase activity. Specifically, *botulinum* toxins belong to the zinc metallopeptidase family, and most particularly to the subfamily of zincins which contain the consensus sequence HExxH (Schiavo et al. (1992) *J. Biol. Chem*. 267(33), 23479–23483). They very specifically cleave neuronal proteins involved in neurotransmitter exocytosis. Thus, syntaxin and SNAP 25 are degraded by *botulinum* toxins A, C and E, whereas synaptobrevin (VAMP) is cleaved by tetanus toxin and *botulinum* toxins B, D, F and G. It is important to note that the site of cleavage of these proteins by the toxins is different, except for BoNT/B and tetanus toxin, which cleave synaptobrevin at the $Q^{76}$—$F^{77}$ bond.

The most effective approach for combating the harmful effects of BoNT/B, either in the course of declared botulism or in the course of therapeutic contraindications, is the development of selective inhibitors with high affinity for its metallopeptidase activity, which is responsible for its toxicity. However, the identification of such inhibitors requires a simple and automatable test for demonstrating BoNT/B activity, allowing a large number of assays.

Now, the tests currently available are not entirely satisfactory. They are either long or relatively insensitive and/or unsuitable for an implementation such as a high throughput screening method.

Currently, the most sensitive method for detecting *botulinum* toxins is based on an in vivo assay in mice (Kautter & Salomon (1976) *J. Assoc. Anal. Chem*. 60, 541–545). This assay makes it possible to detect from 5 to 10 pg of toxin, but the response time is much too long (3–4 days), the serotype of the toxin is not known and, finally, animal experimentation is very controversial. Assays on cell lines have been attempted (DeWaart et al. (1972) *Zentralblatt für Bacteriologie* 222, 96–114), but the sensitivity thereof is too low. Immunoassays have also been proposed, but none shows sufficient sensitivity, even after amplification of the response (Stanley et al. (1985) *J. Immunol. Methods* 83, 89–95; Doellgast et al. (1993) *J. Clin. Microbiol*. 31, 2402–2409). A relatively sensitive calorimetric test has been proposed (Szilaggi et al. (2000) Toxicon 35 381–389) for BoNT/B, but it involves a succession of steps which make it non-automatable.

Other assays currently developed are based on the use of the endopeptidase activity of these toxins (Hallis et al. (1996) *J. Clin. Microbiol*. 34, 1934–1938). This involves cleavage, by BoNT/B, of a fragment of synaptobrevin immobilized on a solid support, and detection, with a specific antibody, of the N-terminal end newly created by cleavage and which remains on the resin. A final protocol consists in immobilizing the toxin on an affinity column. When passed over this column, the substrate is cleaved and the fragment is recognized by an antibody [Witcome et al. (1999) Applied and environmental microbiology 65 3787–3792]. However, these assays have not yet been optimized and are very difficult to automate.

SUMMARY OF THE INVENTION

An object of the present invention is precisely to provide a novel detection test which makes it possible to be free of the drawbacks mentioned above.

In particular, the present invention is based on the demonstration by the inventors that the use of pyrenylalanine (PyA) associated with the modified acid L-para-nitrophenylalanine (pNF) is particularly advantageous both in terms of diagnosis and of determination of inhibitory capacities for the enzymatic activity, able to be adapted to high throughput methods.

Pyrenylalanine is a synthetic amino acid which has a considerable fluorescence capacity. Advantageously, this fluorescence of the PyA residue is virtually completely extinguished when PyA is placed in proximity to the residue pNF. Consequently, this natural fluorescence of PyA can only be expressed once this residue is no longer subjected to the repressor effect of the pNF residue, for example when it is physically separated from the latter, in particular by cleavage of the sequence separating them.

This pairing therefore appears to be a particularly advantageous tool when it is present in a peptide substrate recognized by BoNT/B, in the form of a fragment which can be cleaved by the latter.

A first aspect of the invention therefore relates to a peptide substrate recognized by *botulinum* toxin type BoNT/B, characterized in that it incorporates into its peptide structure a fragment of formula PyA-(Z)-pNF, in which Z represents one or more amino acids, said fragment being cleavable with said toxin.

Figure 1:
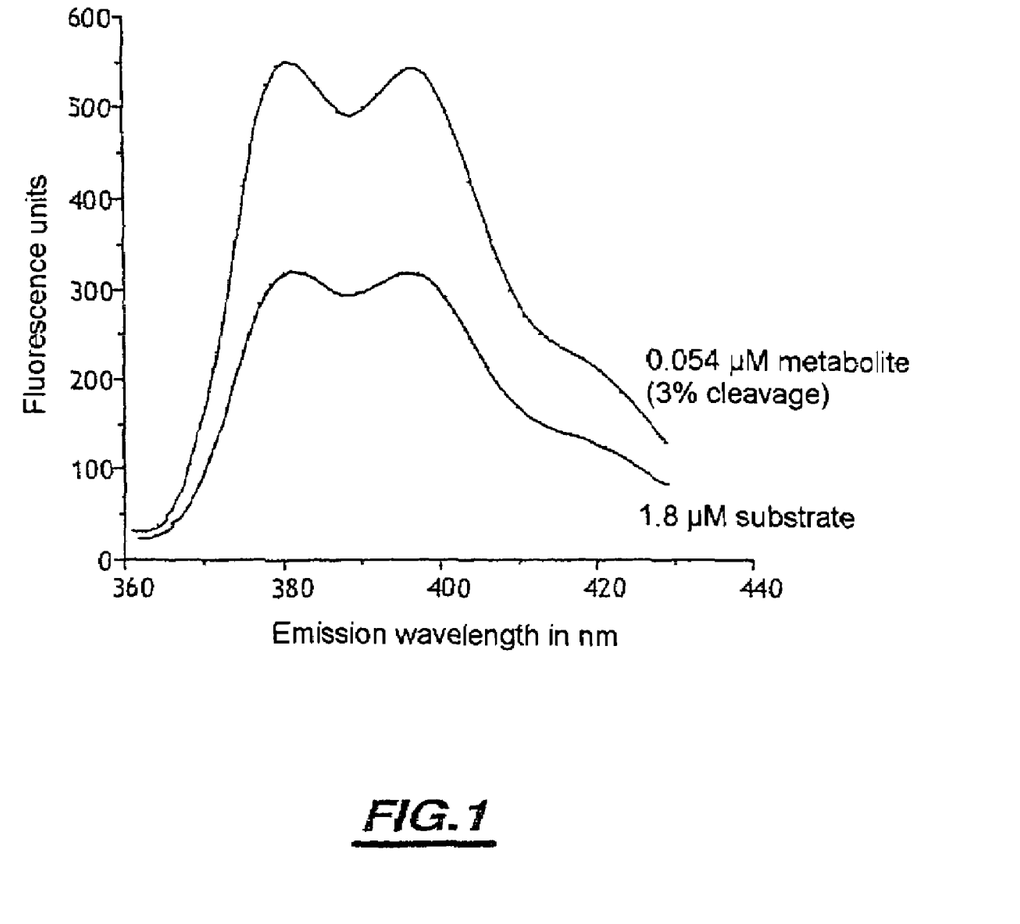
FIG. 1: Emission fluorescence of the metabolites and substrate (excitation at 343 nm).

The present invention is therefore based on the detection of a fluorescence caused by the separation of PyA and pNF, this separation being induced by cleavage of one of the bonds established between them. Cleavage by BoNT/B produces a very strong increase in fluorescence. FIG. 1 illustrates this phenomenon.

Z may thus comprise up to four amino acids, and preferably represents two amino acids, which may be identical or different.

This adjustment is related to the need to preserve the specificity and effectiveness of BoNT/B for cleaving the substrate which includes PyA-(Z)-pNF. The choice of Z is consequently made taking these two criteria into account.

According to a preferred embodiment of the invention, the peptidyl residue PyA-Z-pNF is present, in the peptide sequence of the cellular substrate recognized by BoNT/B, at the cleavage site thereof for which it substitutes.

Preferably, the PyA-(Z)-pNF residue corresponds to the definition PyA-Ser-Gln-pNF (SEQ ID No. 1). This fragment is cleavable with BoNT/B toxin at the Gln-pNF bond.

Preferably, the substrate corresponds to fragment 60–94 of synaptobrevin modified from position 74 and of formula is (SEQ ID No. 2):

(1s)
60
Leu-Ser-Glu-Leu-Asp-Asp-Arg-Ala-Asp-Ala-Leu-Gln-

Ala-Gly-PyA-(Z)-pNF-Glu-Ser-Ala-Ala-Lys-Leu-

Lys-Tyr-Trp-Trp-Lys-Asn-Leu-Lys with Z being as defined above.

The effect of the cleavage is to generate the metabolite of formula 1m (SEQ ID No. 3):

(1m)
60
Leu-Ser-Glu-Leu-Asp-Asp-Arg-Ala-Asp-Ala-Leu-Gln-

74
Ala-Gly-PyA-(Z')

With Z' representing one or more amino acids present in Z.

This metabolite also constitutes one of the subjects of the present invention.

More preferentially, the peptide substrate is the following substrate 2s (SEQ ID No. 4):

(2s)
60
Leu-Ser-Glu-Leu-Asp-Asp-Arg-Ala-Asp-Ala-Leu-Gln-Ala
   74        ↑ 77
Gly-PyA-Ser-Gln—pNF-Glu-Ser-Ala-Ala-Lys-Leu-Lys-
              ↓
           94
Tyr-Trp-Trp-Lys-Asn-Leu-Lys

Selected cleavage thereof at the Gln $^{76}$-pNF$^{77}$ bond by BoNT releases the fluorescent metabolite of formula 2m (SEQ ID No. 5):

(2m)
60
Leu-Ser-Glu-Leu-Asp-Asp-Arg-Ala-Asp-Ala-Leu-Gln-

76
Ala-Gly-PyA-Ser-Gln

The compounds claimed can be obtained by the usual methods of solid-phase synthesis according to the Merrifield method on an automatic synthesizer such as, for example, the 431A synthesizer from Applied Biosystems. The chemistry used corresponds to Fmoc technology and protection of the side chains allowing cleavage thereof with trifluoroacetic acid, as described by E. Atherton and R. C. Sheppard (1989) in "*Solid Phase Peptide Synthesis: a practical approach*, IRL Press, Oxford".

The L-pyrenylalanine is obtained according to a method of asymmetric synthesis described in the publication J. M. Soleilhac et al., *Anal. Biochem.* (1996) 241, 120–127. The purity of the final peptides is estimated to be greater than 99% by reverse-phase HPLC, and they are identified by electrospray mass spectrometry.

The couplings are carried out according to conventional techniques using a coupling agent such as HATU or PyBrop, and preferably using dicyclohexylcarbodiimide/hydroxybenzotriazole.

A substrate in accordance with the present invention is advantageous in several ways.

It can make it possible to rapidly detect the possible presence of *botulinum* toxin type B in a substance. The substrates 1s and 2s in particular exhibit very high selectivity with respect to the other *botulinum* toxins since only BoNT/B cleaves synaptobrevin at the $Q^{76}$—$F^{77}$ bond. It is also very selective with respect to tetanus toxin (Soleilhac et al. (1996) *Anal. Biochem.* 241, 120–127).

It also makes high throughput screening of potential inhibitors of *botulinum* toxin type B possible.

Consequently, the present invention relates to the use of a substrate as defined above, for detecting, identifying and/or assaying BoNT/B or a compound capable of inhibiting or activating BoNT/B.

According to a preferred variant of the invention, the compound to assay is a compound capable of inhibiting BoNT/B.

A subject of the present invention is also a method for detecting, identifying and/or assaying a compound capable of inhibiting BoNT/B, characterized in that it comprises:

bringing a substrate in accordance with the invention into contact, in solution, with said BoNT/B and at least one compound liable to inhibit BoNT/B, measuring the fluorescence emitted in the presence, and/or in the absence, of the compound to be detected, identified and/or assayed, with an absence of, or a decrease in, fluorescence indicating the presence of a compound which inhibits BoNT/B.

A compound to which the test defined above is applied in order to determine its BoNT/B-inhibiting activity may be diverse in nature, without limitation, and will be selected, for example, from recently published inhibitors [L. Martin (1999) *J. Med. Chem.* 42 515–525].

The compound to be tested may be in an isolated form, may be known or unknown, and/or may be present in a library of compounds or a biological extract.

According to a preferred variant, the substrate is:

```
                                          (1s)    (SEQ ID NO:2)
60
Leu-Ser-Glu-Leu-Asp-Asp-Arg-Ala-Asp-Ala-Leu-Gln-Ala
   74
Gly-PyA-(Z)-pNF-Glu-Ser-Ala-Ala-Lys-Leu-Lys-Tyr-

Trp-Trp-Lys-Asn-Leu-Lys
``` and more preferentially

```
                                          (2s)    (SEQ ID NO:4)
60
Leu-Ser-Glu-Leu-Asp-Arg-Ala-Asp-Ala-Leu-Gln-Ala 74           77
Gly-PyA-Ser-Gln↑pNF-Glu-Ser-Ser-Ala-Ala-Lys-Leu-
           ↓
                                                  94
Lys-Arg-Lys-Tyr-Trp-Trp-Lys-Asn-Leu-Lys
```

The addition of increasing doses of a compound capable of inhibiting the enzymatic activity of BoNT/B with respect to a substrate in accordance with the present invention may result in a decrease in the intensity of the fluorescence, due to the decrease in the amount of metabolite formed by the BoNT/B. The measurement of this intensity, related to a standard curve established with mixtures of the substrate and of the fluorescent metabolite formed, therefore makes it possible either to evaluate the inhibitory capacity as percentage inhibition at a set given concentration of the product P, or to precisely determine its $IC_{50}$ and then its $K_i$ using the $K_M$ of the substrate and several concentrations of the product P.

The extreme sensitivity of the assay makes it possible to operate in very small volumes (50 or 100 µl) with concentrations of the order of 20 µM of the substrate 2s. The test can therefore be very easily used in plates containing 96 wells or more, making it possible to automate it with automatic determination of the $K_i$ values when the reading fluorimeter is connected to a computer possessing suitable commercial software.

The present invention therefore provides a test for identifying BoNT/B inhibitors, and also the determination of the inhibitory capacities thereof, using a very rapid, reproducible fluorimetric assay allowing a very large number of tests which can be automated and which can therefore be adapted to high throughput selection of inhibitory molecules.

The present invention also provides the production of novel industrial products, which can optionally be used in the form of kits comprising ready-to-use 96-, 192- and 384-well plates containing either lyophilized BoNT/B or a substrate as defined according to the invention and illustrated in the case of 1s and 2s, to which the reagents required to determine the inhibitory capacities of series of molecules are added, optionally using an automated device.

Another aspect of the invention relates to a method for diagnosing the presence of BoNT/B, in particular in foods which are possibly contaminated, characterized in that it uses a substrate in accordance with the invention, and preferably of 1s type, and more preferentially 2s type.

The figures and examples below are presented by way of nonlimiting illustration of the present invention.

BRIEF DESCRIPTION OF THE FIGURES

Figures.

DETAILED DESCRIPTION

The present invention will now be described with references to the following non-limiting examples.

EXAMPLES

Example 1

Preparation of Peptides

The peptide 2s and its metabolite 2m are prepared in solid phase by the method of Merrifield on an automatic synthesizer using Fmoc strategy and protection of the side chains in the form of t-butyl, trityl or Boc groups, as described in "*Solid Phase Peptide Synthesis: a practical approach*, IRL Press, Oxford (1989)". The L-pyrenylalanine is obtained according to a previously developed method of asymmetric synthesis (*Soleilhac* et al. (1996) *Anal. Biochem.* 241, 120–127). The couplings are carried out using mainly dicyclohexylcarbodiimide/hydroxybenzotriazole in N-methylpyrrolidone. HATU in the presence of diisopropylethylamine can advantageously be used to introduce the pyrenylalanine into the peptide sequence. The final peptide is obtained after cleavage of the resin and deprotection of the side chains with trifluoroacetic acid. The solution is evaporated under vacuum and the peptide is precipitated in ether at −20° C. and purified by HPLC on a $C_8$ nucleosil column. The peptides are analyzed by mass spectrometry and 1H NMR (600 MHz).

Compound 2s:

```
60
Leu-Ser-Glu-Leu-Asp-Asp-Arg-Ala-Asp-Ala-Leu-Gln-Ala

74          ↑77
Gly-PyA-Ser-Gln↑pNF-Glu-Ser-Ser-Ala-Ala-Lys-Leu-
           ↓
                                                 94
Lys-Arg-Lys-Tyr-Trp-Trp-Lys-Asn-Leu-Lys
```

$MH^+_{(exp)}$4269.04 $MH^+_{(theo)}$4269.20

Compound 2m:

```
                                          (SEQ ID NO:5)
60
Leu-Ser-Glu-Leu-Asp-Asp-Arg-Ala-Asp-Ala-Leu-Gln-Ala

76
Gly-PyA-Ser-Gln
```

$MH^+_{(exp)}$1959.83 $MH^+_{(theo)}$1958.06

The *botulinum* toxin type B used for high throughput tests corresponds to the light chain of BoNT/B, which is commercially available (Sigma, France Biochem). It can also be isolated by cleavage of the whole protein (light and heavy chains) produced by strains of *clostridium botulinum* type B.

Example 2

Fluorimetric Assay

Figure 2:
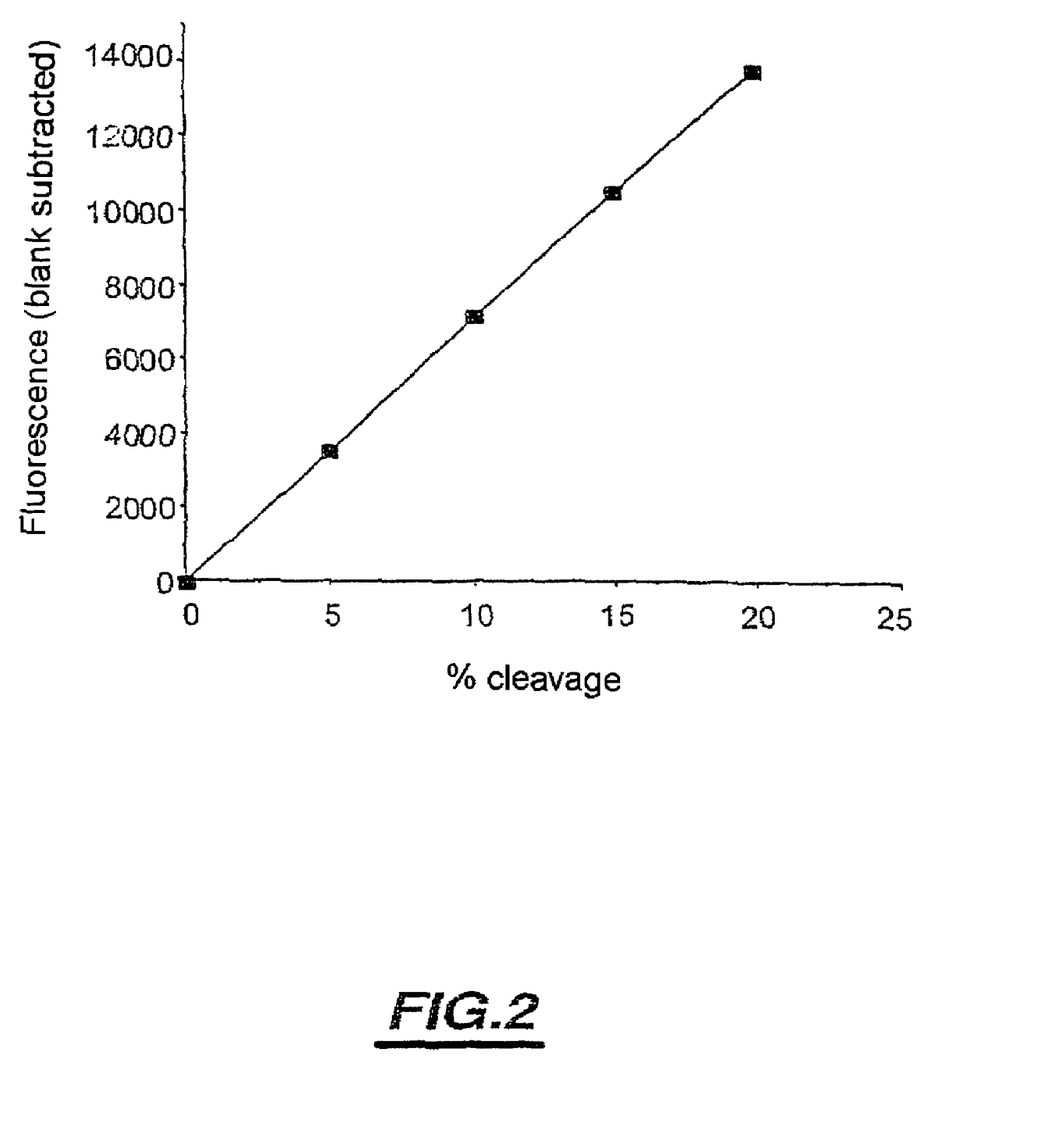
FIG. 2: Measurement of the kinetic constants of the substrate.

The substrate 2s (18 µM) is incubated for 30 minutes with 0.35 ng of BoNT/B light chain at 37° C. in 100 µl of 20 mM HEPES buffer, pH 7.4, containing 0.1 mM of DTT. The enzymatic hydrolysis is stopped by adding 100 µl of 0.2 N HCl, and the fluorescence emitted is read directly on a fluorimeter ($\lambda_{ex}$ 343 nm, $\lambda_{em}$ 377 nm). Under these conditions, less than 10% substrate cleavage is obtained (FIG. 2).

Identification of the cleavage site by HPLC.

Solutions of the substrate 2s before and after incubation with the enzyme under the standard conditions described above are analyzed by HPLC on a 7 µm/300 Å (4.6×70 mm) $C_8$ nucleosil column with, as eluent, a 10–90% gradient of solvent B in 30 minutes (solvent A: 0.05% trifluoroacetic acid in water; solvent B: 0.038% trifluoroacetic acid in 90/10 $CH_3CN/H_2O$). UV or fluorimetric detection, retention time of the substrate S: 15.90 min; metabolite M: 12.76 min.

Measurement of the kinetic constants of the substrate.

0.23 ng of BoNT/B light chain and varying concentrations (from 3.9 to 500 µM) of substrate S are incubated for 30 minutes, at 37° C., in 100 µl of 20 mM HEPES buffer, pH 7.4, containing 0.1 mM DTT. The reaction is stopped as described above. For each concentration of substrate, a calibration curve representing 5, 10, 15 and 20% cleavage is established by mixing the substrate S and its fluorescent metabolite M (FIG. 2).

The percentage cleavage should always be less than 10%.

Based on these calibration curves, the amounts of metabolites formed for each assay are determined and the Km values are calculated using the Enzfitter program (Biosoft); $K_M$=47 µM; $k_{cat}$=45 s$^{-1}$.

Example 3

Assaying of Minimal Amounts of BoNT/B in a Sample

Figure 3:
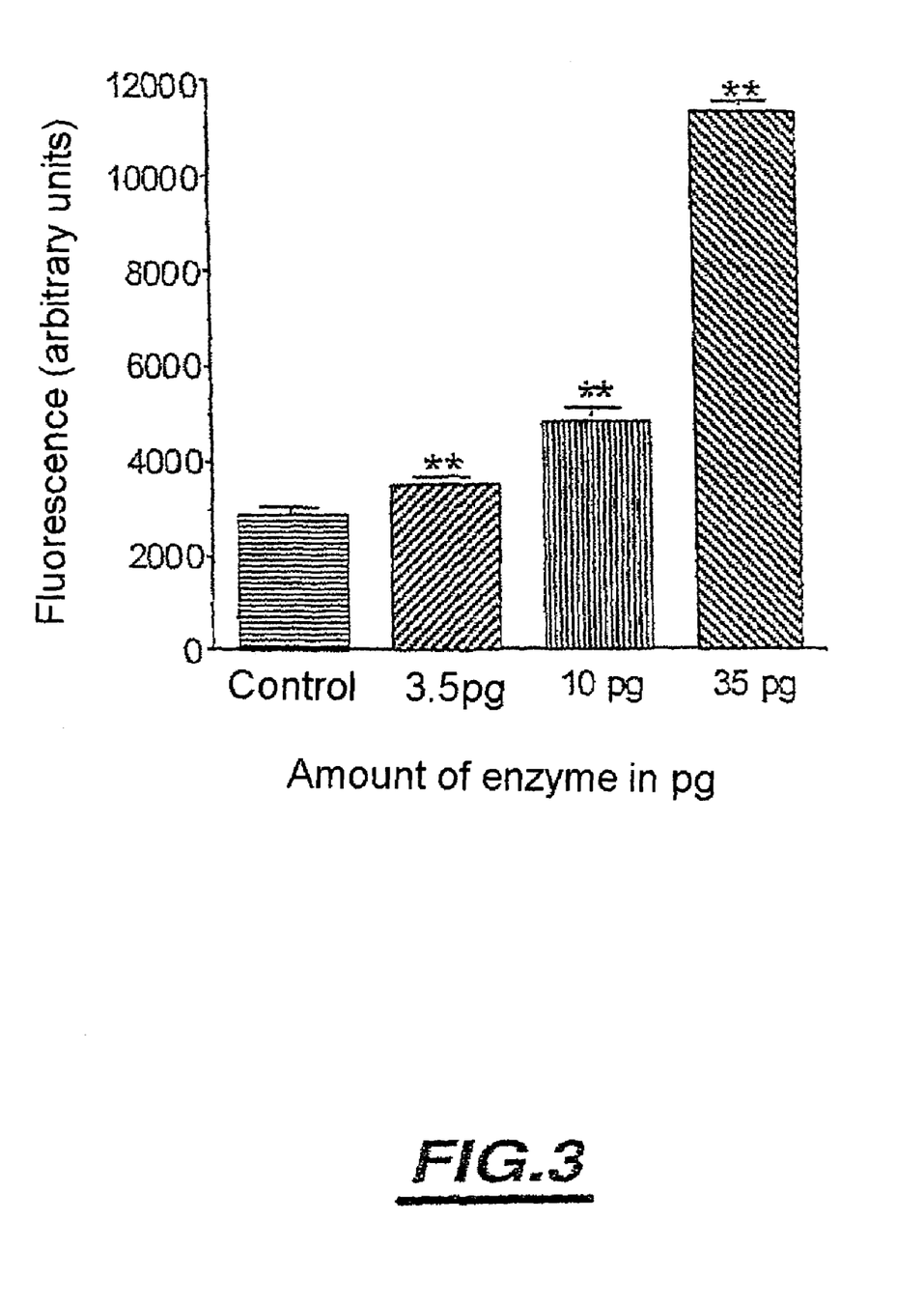
FIG. 3: Fluorescence as a function of the amount of enzyme.

The substrate 2s (18 µM) and increasing amounts (3.5 pg, 10 pg and 35 pg) of BoNT/B light chain are incubated for 4 h, at 37° C., in 20 mM HEPES buffer, pH 7.4, containing 0.1 mM DTT. Analysis of the fluorescence due to degradation of the substrate in the presence of 3.5 pg of toxin is reproducible and significantly different (p=0.01) than that of the control containing only the substrate 2s (FIG. 3).

Example 4

Determination of the $K_i$ of BoNT/B Inhibitors

This assay can be automated on a 96-well plate. Increasing amounts of inhibitors selected from L. Martin et al. (1999), J. Med. Chem. 42, 515–525, and 0.35 ng of BoNT/B light chain are preincubated in a final volume of 100 µl of 20 mM HEPES buffer containing 0.1 mM DTT, for 30 minutes. 18 µM of substrate 2s are then added, and the incubation is continued for 30 minutes at 37° C. The reaction is stopped by adding 0.2 M HCl and the plate is read directly on a fluorimeter.

The amount of metabolite formed in each assay is determined from the standard curves.

Figure 4:
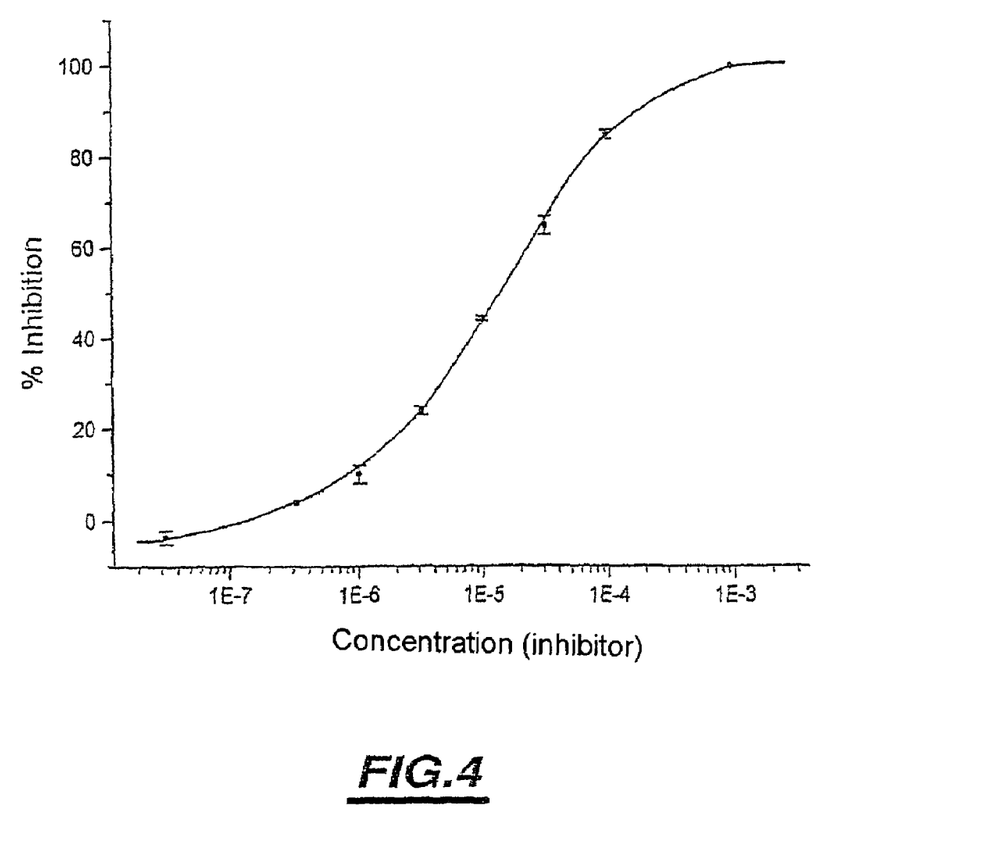
FIG. 4: Determination of the Ki of the compound 2s in L. Martin et al. (1999), J. Med. Chem. 42, 515–525) on BoNT/B.
Ki(BoNT/B)=5.6 $10^{-6}$M.

The $K_i$ of the inhibitor is determined using the Cheng-Prusoff equation: $K_i$=$IC_{50}$/(1+[S]/$K_M$) (FIG. 4).

The invention claimed is:

1. A peptide substrate recognized by *botulinum* toxin type BoNT/B, which has the formula 2s:
   Leu-Ser-Glu-Leu-Asp-Asp-Arg-Ala-Asp-Ala-Leu-Gln-Ala Gly-PyA-Ser-Gln-pNF-Glu-Ser-Ser-Ala-Ala-Lys-Leu-Lys-Arg-Lys-Tyr-Trp-Trp-Lys-Asn-Leu-Lys (2s) (SEQ ID NO:4).

2. A compound of formula 2m:
   Leu-Ser-Glu-Leu-Asp-Asp-Arg-Ala-Asp-Ala-Leu-Gln-Ala Gly-PyA-Ser-Gln (2m) (SEQ ID NO:5).

3. A method for detecting, identifying and/or assaying a compound capable of inhibiting or activating BoNT/B, which comprises:
   contacting a substrate as claimed in claim 1, in solution, with BoNT/B and, optionally with at least a compound likely to inhibit or activate BoNT/B; and
   measuring the fluorescence emitted in the presence, and in the absence, of the compound to be detected, identified and/or assayed;
   wherein an absence of, or a decrease in the fluorescence emitted in the presence of the compound to be detected, identified and/or assayed as compared with the fluorescence emitted in the absence of the compound, indicates the presence of a compound which inhibits BoNT/B, and
   wherein an increase in the fluorescence emitted in the presence of the compound to be detected, identified and/or assayed as compared with the fluorescence emitted in the absence of the compound indicates the presence of a compound which activates BoNT/B.

4. The method according to claim 3, wherein the compound to be tested is present in a library of compounds or a biological extract.

5. A method for identifying the presence of BoNT/B in a sample, which comprises the steps consisting of:
   contacting said sample with a peptide substrate according to claim 1; and
   measuring the fluorescence emitted by the peptide substrate in the presence of the sample, and measuring the fluorescence emitted by the peptide substrate alone;
   wherein an increase in fluorescence emitted by the peptide substrate in the presence of the sample, as compared with the fluorescence emitted by the peptide substrate alone, indicates the presence of BoNT/B in the sample.

6. The method according to claim 5, wherein the sample is a food sample.

* * * * *

UNITED STATES PATENT AND TRADEMARK OFFICE
CERTIFICATE OF CORRECTION

PATENT NO.       : 7,160,982 B2
APPLICATION NO. : 10/296396
DATED            : January 9, 2007
INVENTOR(S)      : Roques et al.

It is certified that error appears in the above-identified patent and that said Letters Patent is hereby corrected as shown below:

On Title Page Item (73) Assignee: change "Institut National de la Santa et de la Rescherche Medicale (Inserm)" to -- Institut National de la Sante et de la Recherche Medicale (Inserm), Paris (FR); and Centre National de la Recherche Scientifique (C.N.R.S.), Paris, (FR) --.

Signed and Sealed this

Tenth Day of April, 2007

JON W. DUDAS
*Director of the United States Patent and Trademark Office*

SEQUENCE LISTING

```
<160> NUMBER OF SEQ ID NOS: 5

<210> SEQ ID NO 1
<211> LENGTH: 4
<212> TYPE: PRT
<213> ORGANISM: ARTIFICIAL
<220> FEATURE:
<223> OTHER INFORMATION: Artificial peptide used as a substrate
<220> FEATURE:
<221> NAME/KEY: MISC_FEATURE
<222> LOCATION: (1)..(1)
<223> OTHER INFORMATION: Xaa = PyA
<220> FEATURE:
<221> NAME/KEY: MISC_FEATURE
<222> LOCATION: (4)..(4)
<223> OTHER INFORMATION: Xaa = pNF

<400> SEQUENCE: 1

Xaa Ser Gln Xaa
1

<210> SEQ ID NO 2
<211> LENGTH: 31
<212> TYPE: PRT
<213> ORGANISM: ARTIFICIAL
<220> FEATURE:
<223> OTHER INFORMATION: Artificial peptide used as a substrate
<220> FEATURE:
<221> NAME/KEY: MISC_FEATURE
<222> LOCATION: (15)..(15)
```

```
<223> OTHER INFORMATION: Xaa = PyA
<220> FEATURE:
<221> NAME/KEY: MISC_FEATURE
<222> LOCATION: (16)..(16)
<223> OTHER INFORMATION: Xaa = Z
<220> FEATURE:
<221> NAME/KEY: MISC_FEATURE
<222> LOCATION: (17)..(17)
<223> OTHER INFORMATION: Xaa =pNF

<400> SEQUENCE: 2

Leu Ser Glu Leu Asp Asp Arg Ala Asp Ala Leu Gln Ala Gly Xaa Xaa
1               5                   10                  15

Xaa Glu Ser Ala Ala Lys Leu Lys Tyr Trp Trp Lys Asn Leu Lys
            20                  25                  30

<210> SEQ ID NO 3
<211> LENGTH: 16
<212> TYPE: PRT
<213> ORGANISM: ARTIFICIAL
<220> FEATURE:
<223> OTHER INFORMATION: Artificial peptide used as a metabolite
<220> FEATURE:
<221> NAME/KEY: MISC_FEATURE
<222> LOCATION: (15)..(15)
<223> OTHER INFORMATION: Xaa = PyA
<220> FEATURE:
<221> NAME/KEY: MISC_FEATURE
<222> LOCATION: (16)..(16)
<223> OTHER INFORMATION: Xaa = Z'

<400> SEQUENCE: 3

Leu Ser Glu Leu Asp Asp Arg Ala Asp Ala Leu Gln Ala Gly Xaa Xaa
1               5                   10                  15

<210> SEQ ID NO 4
<211> LENGTH: 32
<212> TYPE: PRT
<213> ORGANISM: ARTIFICIAL
<220> FEATURE:
<223> OTHER INFORMATION: Artificial peptide used as a substrate
<220> FEATURE:
<221> NAME/KEY: MISC_FEATURE
<222> LOCATION: (15)..(15)
<223> OTHER INFORMATION: Xaa = PyA
<220> FEATURE:
<221> NAME/KEY: MISC_FEATURE
<222> LOCATION: (18)..(18)
<223> OTHER INFORMATION: Xaa = pNF

<400> SEQUENCE: 4

Leu Ser Glu Leu Asp Asp Arg Ala Asp Ala Leu Gln Ala Gly Xaa Ser
1               5                   10                  15

Gln Xaa Glu Ser Ala Ala Lys Leu Lys Tyr Trp Trp Lys Asn Leu Lys
            20                  25                  30

<210> SEQ ID NO 5
<211> LENGTH: 17
<212> TYPE: PRT
<213> ORGANISM: ARTIFICIAL
<220> FEATURE:
<223> OTHER INFORMATION: Artificial peptide used as a metabolite
<220> FEATURE:
<221> NAME/KEY: MISC_FEATURE
<222> LOCATION: (15)..(15)
<223> OTHER INFORMATION: Xaa = PyA
```

```
<400> SEQUENCE: 5

Leu Ser Glu Leu Asp Asp Arg Ala Asp Ala Leu Gln Ala Gly Xaa Ser
1               5                   10                  15
Gln
```